(12) United States Patent
Yamada et al.

(10) Patent No.: US 8,921,271 B2
(45) Date of Patent: Dec. 30, 2014

(54) HERBICIDAL COMPOSITION COMPRISING FLAZASULFURON AND METRIBUZIN

(75) Inventors: Ryu Yamada, Kusatsu (JP); Hiroyuki Okamoto, Kusatsu (JP); Takashi Terada, Kusatsu (JP)

(73) Assignee: Ishihara Sangyo Kaisha, Ltd., Osaka (JP)

( * ) Notice: Subject to any disclaimer, the term of this patent is extended or adjusted under 35 U.S.C. 154(b) by 0 days.

(21) Appl. No.: 14/110,289

(22) PCT Filed: Apr. 6, 2012

(86) PCT No.: PCT/JP2012/060091
§ 371 (c)(1),
(2), (4) Date: Dec. 19, 2013

(87) PCT Pub. No.: WO2012/141277
PCT Pub. Date: Oct. 18, 2012

(65) Prior Publication Data
US 2014/0128263 A1 May 8, 2014

(30) Foreign Application Priority Data
Apr. 14, 2011 (JP) ................................. 2011-090116

(51) Int. Cl.
*A01N 47/36* (2006.01)
*A01N 43/707* (2006.01)
*A01N 43/54* (2006.01)

(52) U.S. Cl.
CPC ............. *A01N 43/707* (2013.01); *A01N 47/36* (2013.01); *A01N 43/54* (2013.01)
USPC ......................................... 504/134; 504/136

(58) Field of Classification Search
USPC .................................................. 504/134, 136
See application file for complete search history.

(56) References Cited

U.S. PATENT DOCUMENTS

| 5,990,048 A | 11/1999 | Dahmen et al. | |
| 6,316,386 B1 | 11/2001 | Dahmen et al. | |
| 6,486,096 B1 | 11/2002 | Hacker et al. | |
| 8,633,135 B2 * | 1/2014 | Kikugawa et al. | 504/136 |
| 2001/0056040 A1 | 12/2001 | Dahmen et al. | |
| 2009/0069346 A1 | 3/2009 | Ishihara et al. | |
| 2011/0190136 A1 * | 8/2011 | Hufnagl et al. | 504/136 |
| 2014/0121108 A1 * | 5/2014 | Yamada et al. | 504/136 |
| 2014/0128263 A1 * | 5/2014 | Yamada et al. | 504/134 |

FOREIGN PATENT DOCUMENTS

| CN | 1398517 A | 2/2003 |
| DE | 196 38 887 A1 | 3/1998 |
| JP | 2007-262052 A | 10/2007 |
| WO | 00/08932 A1 | 2/2000 |
| WO | 2007/105377 | 9/2007 |

OTHER PUBLICATIONS

Search Report from International Application No. PCT/JP2012/060091, mail date is Mar. 7, 2012.
K. Umeda et al., "Comparison of Sulfonylurea Herbicides for Spring Transition", University of Arizona College of Argiculture 2004 Turfgrass and Oranamental Research Report, Dec. 1, 2004, pp. 1-9.
International Preliminary Report on Patentability for International Patent Application No. PCT/JP2012/060091, mail date is Oct. 24, 2013.

* cited by examiner

*Primary Examiner* — John Pak
(74) *Attorney, Agent, or Firm* — Greenblum & Bernstein, P.L.C.

(57) ABSTRACT

Many herbicidal compositions have been developed and are presently used. However, weeds to be controlled are various in types and their emergence extends over a long period. Accordingly, it is desired to develop a herbicidal composition which has a broader herbicidal spectrum, a high activity and a long-lasting effect.

The present invention provides a herbicidal composition comprising, as active ingredients, (a) flazasulfuron or its salt and (b) metribuzin or its salt.

6 Claims, 1 Drawing Sheet

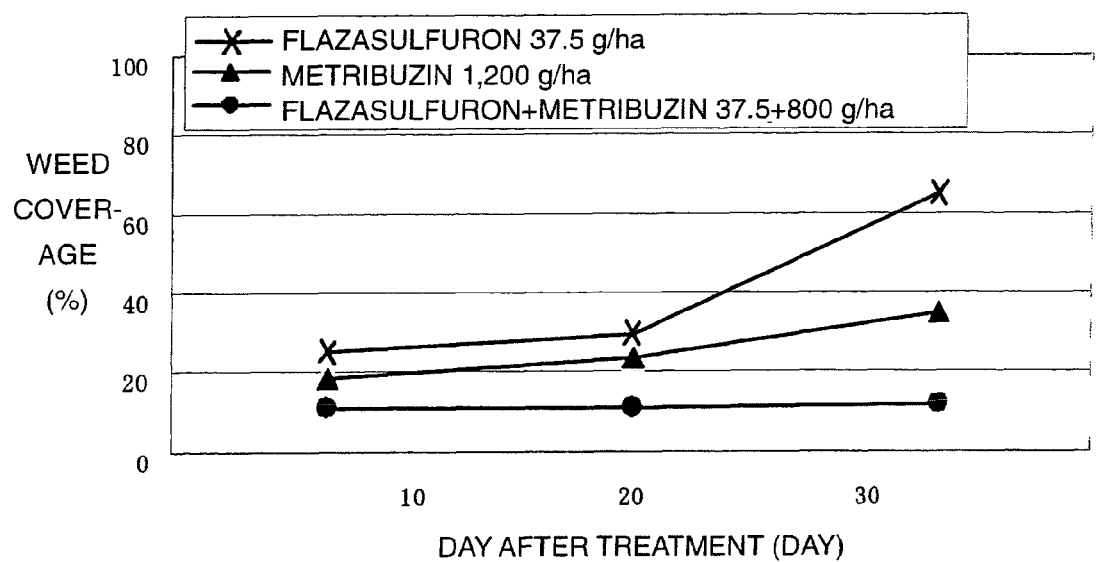

HERBICIDAL COMPOSITION COMPRISING FLAZASULFURON AND METRIBUZIN

TECHNICAL FIELD

The present invention relates to a herbicidal composition comprising (a) flazasulfuron or its salt and (b) metribuzin or its salt.

BACKGROUND ART

Patent Document 1 discloses a solid herbicidal composition comprising flazasulfuron or its salt and a certain surfactant. However, Patent Document 1 failed to disclose specific combination of the herbicidal composition of the present invention, nor synergistic effects obtainable by the combination.

PRIOR ART DOCUMENT

Patent Document

Patent Document 1: JP-A-2007-262052

DISCLOSURE OF INVENTION

Technical Problem

Many herbicidal compositions have been developed and are presently used, but they are not necessarily satisfactory in some cases to control noxious plants such as weeds to be controlled, and it is desired to develop a highly active herbicidal composition.

Weeds to be controlled are many in types and their emergence extends over a long period, and therefore, it is desired to develop a herbicidal composition having a broader herbicidal spectrum and a long-lasting effect (hereinafter sometimes referred to as residual activity). Further, recently, with a view to reducing an environmental load on a place where a herbicidal agent is applied or a peripheral area thereof, it is desired to develop a technique of reducing the dose of the active ingredient.

Solution to Problem

The present inventors have conducted a research to solve the above problem, etc., and as a result, have found a practically highly useful herbicidal composition. That is, the present invention provides a highly active herbicidal composition comprising, as active ingredients, (a) flazasulfuron or its salt and (b) metribuzin or its salt. Further, the present invention relates to a method for controlling noxious plants, which comprises applying a herbicidally effective amount of the above herbicidal composition to the noxious plants or to a place where they grow. Further, the present invention provides a method for controlling noxious plants, which comprises applying a herbicidally effective amount of (a) and a herbicidally effective amount of (b), to the noxious plants or to a place where they grow.

Advantageous Effects of Invention

According to the present invention, it is possible to provide a highly active herbicidal composition having a long-lasting effect, and capable of reducing the dose of the active ingredients.

The herbicidal composition of the present invention is capable of controlling a wide range of noxious plants emerging in agricultural fields or non-agricultural fields. It surprisingly presents a synergistic herbicidal effect i.e. a herbicidal effect higher than the mere addition of the respective herbicidal effects of the active ingredients. Such a herbicidal composition of the present invention can be applied at a low dose as compared with a case where the respective active ingredients are applied individually. Thus, it is effective to reduce the environmental load on an area where the composition is applied or a surrounding area thereof.

When the herbicidal activity in a case where two active ingredients are combined, is larger than the simple sum of the respective herbicidal activities of the two active ingredients (the expected activity), it is called a synergistic effect. The activity expected by the combination of two active ingredients can be calculated as follows (Colby S. R., "Weed", vol. 15, p. 20-22, 1967).

$$E = \alpha + \beta - (\alpha \times \beta \div 100)$$

where
$\alpha$: growth inhibition rate when treated with x (g/ha) of herbicide X,
$\beta$: growth inhibition rate when treated with y (g/ha) of herbicide Y,
E: growth inhibition rate expected when treated with x (g/ha) of herbicide X and y (g/ha) of herbicide Y.

That is, when the actual growth inhibition rate (measured value) is larger than the growth inhibition rate by the above calculation (calculated value), the activity by the combination can be regarded as showing a synergistic effect. The herbicidal composition of the present invention shows a synergistic effect when calculated by the above formula.

BRIEF DESCRIPTION OF DRAWING

FIG. 1 is a graph illustrating the comparison of the residual activity among the area treated with flazasulfuron, the area treated with metribuzin and the area treated with flazasulfuron and metribuzin in combination.

DESCRIPTION OF EMBODIMENTS

In the above (a), flazasulfuron (common name) is 1-(4,6-dimethoxypyrimidin-2-yl)-3-(3-trifluoromethyl-2-pyridylsulfonyl)urea.

In the above (b), metribuzin (common name) 4-amino-6-tertiary butyl-3-methylthio-1,2,4-triazin-5(4H)-one.

The salt included in the above (a) or (b) may be any salt so long as it is agriculturally acceptable. Examples thereof include alkali metal salts such as a sodium salt and a potassium salt; alkaline earth metal salts such as a magnesium salt and a calcium salt; ammonium salts such as a monomethylammonium salt, a dimethylammonium salt and a triethylammonium salt; inorganic acid salts such as a hydrochloride, a perchlorate, a sulfate and a nitrate, and organic acid salts such as an acetate and a methanesulfonate.

The mixing ratio of the above (a) to (b) in the present invention cannot generally be defined, as it may vary depending upon various conditions such as the types of compounds to be mixed, the type of the formulation, the weather conditions, and the type and the growth stage of the noxious plants to be controlled, but it is usually from 1:300 to 1:1, preferably from 1:133 to 1:3 by the weight ratio of (a):(b).

The herbicidally effective amounts of the above (a) and (b) in the present invention cannot generally be defined, as they may vary depending upon the various conditions such as the mixing ratio of (a) to (b), the type of the formulation, the weather conditions, and the type and the growth stage of the noxious plants to be controlled. However, (a) is applied in an amount of usually from 10 to 200 g/ha, preferably from 15 to 100 g/ha, and (b) is applied in an amount of usually from 200 to 3,000 g/ha, preferably from 300 to 2,000 g/ha.

The herbicidal composition of the present invention may be applied to noxious plants or may be applied to a place where they grow. Further, it may be applied at any time either before or after the emergence of the noxious plants. Further, the herbicidal composition of the present invention may take various application forms such as soil application, foliar application, irrigation application, and submerged application, and it can be applied to agricultural fields such as upland fields, orchards and paddy fields, and non-cropland such as ridges of fields, fallow fields, play grounds, golf courses, vacant lands, forests, factory sites, railway sides and roadsides.

The herbicidal composition of the present invention can control a broad range of noxious plants such as annual weeds and perennial weeds. The noxious plants to be controlled by the herbicidal composition of the present invention may, for example, be cyperaceae such as green kyllinga (*Kyllinga brevifolia* Rottb. var. *leiolepis*), or sedge (*Cyperus* spp.) [the sedge may, for example, be purple nutsedge (*Cyperus rotundus* L.), smallflower umbrella sedge (*Cyperus difformis* L.), yellow nutsedge (*Cyperus esculentus* L.) or amur *cyperus* (*Cyperus microiria* Steud.)]; gramineae such as barnyardgrass (*Echinochloa crus-galli* L., *Echinochloa oryzicola* vasing.), crabgrass (*Digitaria* spp.) [the crabgrass may, for example, be summergrass (*Digitaria ciliars* (Retz.) Koel), large crabgrass (*Digitaria sanguinalis* L.), violet crabgrass (*Digitaria violascens* Link) or *Digitaria horizontalis* Willd.], green foxtail (*Setaria viridis* L.), giant foxtail (*Setaria faberi* Herrm.), goosegrass (*Eleusine indica* L.), johnsongrass (*Sorghum halepense* (L.) Pers.), annual bluegrass (*Poa annua* L.), panic grass (*Panicum* spp.) [the panic grass may, for example, be guinea grass (*Panicum maximum* Jacq.), or fall *panicum* (*Panicum dichotomiflorum* (L.) Michx.)], signal grass (*Brachiaria* spp.) [the signal grass may, for example, be plantain signal grass (*Brachiaria plantaginea* (LINK) Hitchc.), palisade signal grass (*Brachiaria decumbens* Stapf), or mauritius signal grass (*Brachiaria mutica* (Forssk.) Stapf)], paspalum (*Paspalum* spp.), itchgrass (*Rottboellia cochinchinensis* (LOUR.) W. D. CLAYTON), or shattercane (*Sorghum bicolor* (L.) Moench.); scrophulariaceae such as persian speedwell (*Veronica persica* Poir.), or corn speedwell (*Veronica arvensis* L.); compositae such as beggar ticks (*Bidens* spp.) [the beggar ticks may, for example, be hairy beggarticks (*Bidens pilosa* L.), devils berggarticks (*Bidens frondosa* L.), *Bidens bitemata* (Lour.) Merr. et Sherff), or beggarticks (*Bidens subalternans* DC.)], hairy fleabane (*Conyza bonariensis* (L.) Cronq.), horseweed (*Erigeron canadensis* L.), dandelion (*Taraxacum officinale* Weber), or common cocklebur (*Xanthium strumarium* L.); leauminosae such as white clover (*Trifolium repens* L.); caryophyllaceae such as sticky chickweed (*Cerastium glomeratum* Thuill.), or common chickweed (*Stellara media* L.); euphorbiaceae such as garden spurge (*Euphorbia hirta* L.), threeseeded copperleaf (*Acalypha australis* L.), or fireplant (*Euphorbia heterophylla* L.); plantaginaceae such as asiatic plantain (*Plantago asiatica* L.); oxalidaceae such as creeping woodsorrel (*Oxalis corniculata* L.); apiaceae such as lawn pennywort (*Hydrocotyle sibthorpioides* Lam.); violaceae such as violet (*Viola mandshurica* W. Becker); iridaceae such as blue-eyedgrass (*Sisyrinchium rosulatum* Bicknell); aeraniaceae such as carolina geranium (*Geranium carolinianum* L.); labiatae such as purple deadnettle (*Lamium purpureum* L.), or henbit (*Lamium amplexicaule* L.); malvaceae such as velvetleaf (*Abutilon theophrasti* MEDIC.), or prickly *sida* (*Sida spinosa* L.); convolvulaceae such as ivy-leaved momingglory (*Ipomoea hederace* a (L.) Jacq.), common momingglory (*Ipomoea purpurea* ROTH), cypressvine momingglory (*Ipomoea quamoclit* L.), *Ipomoea grandifolia* (DAMMERMANN) O'DONNELL, hairy *merremia* (*Merremia aegyptia* (L.) URBAN), or field Bindweed (*Convolvulus arvensis* L.); chenopodiaceae such as common lambsquarters (*Chenopodium album* L.); portulacaceae such as common purslane (*Portulaca oleracea* L.); amaranthaceae such as pigweed (*Amaranthus* spp.) [the pigweed may, for example, be prostrate pigweed (*Amaranthus blitoides* S. Wats.), livid amaranth (*Amaranthus lividus* L.), purple amaranth (*Amaranthus blitum* L.), smooth pigweed (*Amaranthus hybridus* L.), *Amaranthus patulus* Bertol., powell amaranth (*Amaranthus powellii* S. Wats.), slender amaranth (*Amaranthus viridis* L.), palmer amaranth (*Amaranthus palmed* S. Wats.), redroot pigweed (*Amaranthus retroflexus* L.), tall waterhemp (*Amaranthus tuberculatus* (Moq.) Sauer.), common waterhemp (*Amaranthus tamariscinus* Nutt.), thorny amaranth (*Amaranthus spinosus* L.), ataco (*Amaranthus quitensis* Kunth.), or *Amaranthus rudis* Sauer]; solanaceae such as black nightshade (*Solanum nigrum* L.); polygonaceeae such as spotted knotweed (*Polygonum lapathifolium* L.), or green smartweed (*Polygonum scabrum* MOENCH); cruciferae such as flexuous bittercress (*Cardamine flexuosa* WITH.); cucurbitaceae such as burcucumber (*Sicyos angulatus* L.); or commelinaceae such as common dayflower (*Commelina communis* L.).

The herbicidal composition of the present invention is effectively used to selectively control noxious weeds in cultivation of various transformed plants. Examples of the transformed plants include pest-resistant transformed plants, phytopathogen-resistant transformed plants, transformed plants regarding plant components, and herbicide-tolerant transformed plants.

By use of the above (a) and (b) in combination in the present invention, a remarkable improvement in residual activity, which is unexpected from effects when the respective active ingredients are applied individually, can be achieved.

Further, the herbicidal composition of the present invention is very useful in a practical application, since it is capable of controlling, for example, strongly noxious weeds in sugarcane fields, such as convolvulaceae (such as ivy-leaved momingglory, common momingglory, cypressvine momingglory, *Ipomoea grandifolia* (DAMMERMANN) O'DONNELL, hairy *merremia*, field Bindweed, or the like), cyperaceae (such as purple nutsedge, yellow nutsedge, or the like) or gramineae (such as crabgrass, panic grass, signal grass, johnsongrass, or the like). Here, the crabgrass is specifically summergrass, large crabgrass, violet crabgrass, *Digitaria horizontalis* Willd., or the like; the panic grass is specifically guinea grass, fall *panicum*, or the like; and the signal grass is specifically plantain signal grass, palisade signal grass, mauritius signal grass, or the like.

The herbicidal composition of the present invention may further contain other herbicidal compounds in addition to the above-described active ingredients so long as such will meet the object of the present invention, and there may be a case where it is thereby possible to improve e.g. the range of weeds to be controlled, the timing for application of the herbicidal composition, the herbicidal activities, etc. to more desirable directions. Such other herbicidal compounds include, for example, the following compounds (common names including ones under application for approval by ISO, or test codes, here, "under application for approval by ISO" means common names before approval by ISO (Intentional Organization for Standardization)), and one or more of them may suitably be selected for use. Even when not specifically mentioned here, in a case where such compounds have salts, alkyl esters, hydrates, different crystal forms, various structural isomers, etc., they are, of course, all included.

Further, in consideration of the application site of the herbicidal composition or the type or growth state of the noxious plants, the herbicidal composition of the present invention may be mixed with or may be used in combination with fungicides, antibiotics, plant hormones, insecticides, fertilizers, phytotoxicity-reducing agents, etc., whereby more excellent effects and activities may sometimes be obtained.

(1) Those which are believed to exhibit herbicidal effects by disturbing hormone activities of plants, such as a phenoxy type such as 2,4-D, 2,4-D-butotyl, 2,4-D-butyl, 2,4-D-dimethylammonium, 2,4-D-diolamine, 2,4-D-ethyl, 2,4-D-2-ethylhexyl, 2,4-D-isobutyl, 2,4-D-isoctyl, 2,4-D-isopropyl, 2,4-D-isopropylammonium, 2,4-D-sodium, 2,4-D-isopropanolammonium, 2,4-D-trolamine, 2,4-DB, 2,4-DB-butyl, 2,4-DB-dimethylammonium, 2,4-DB-isoctyl, 2,4-DB-potassium, 2,4-DB-sodium, dichlorprop, dichlorprop-butotyl, dichlorprop-dimethylammonium, dichlorprop-isoctyl, dichlorprop-potassium, dichlorprop-P, dichlorprop-P-dimethylammonium, dichlorprop-P-potassium, dichlorprop-P-sodium, MCPA, MCPA-butotyl, MCPA-dimethylammonium, MCPA-2-ethylhexyl, MCPA-potassium, MCPA-sodium, MCPA-thioethyl, MCPB, MCPB-ethyl, MCPB-sodium, mecoprop, mecoprop-butotyl, mecoprop-sodium, mecoprop-P, mecoprop-P-butotyl, mecoprop-P-dimethylammonium, mecoprop-P-2-ethylhexyl, mecoprop-P-potassium, naproanilide or clomeprop; an aromatic carboxylic acid type such as 2,3,6-TBA, dicamba, dicamba-butotyl, dicamba-diglycolamine, dicamba-dimethylammonium, dicamba-diolamine, dicamba-isopropylammonium, dicamba-potassium, dicamba-sodium, dichlobenil, picloram, picloram-dimethylammonium, picloram-isoctyl, picloram-potassium, picloram-triisopropanolammonium, picloram-triisopropylammonium, picloram-trolamine, triclopyr, triclopyr-butotyl, triclopyr-triethylammonium, clopyralid, clopyralid-olamine, clopyralid-potassium, clopyralid-triisopropanolammonium or aminopyralid; and others such as naptalam, naptalam-sodium, benazolin, benazolin-ethyl, quinclorac, quinmerac, diflufenzopyr, diflufenzopyr-so sodium, fluroxypyr, fluroxypyr-2-butoxy-1-methylethyl, fluroxypyr-meptyl, chlorflurenol, chlorflurenol-methyl, aminocyclopyrachlor, aminocyclopyrachlor-methyl or aminocyclopyrachlor-potassium.

(2) Those which are believed to exhibit herbicidal effects by inhibiting photosynthesis of plants, such as a urea type such as chlorotoluron, diuron, fluometuron, linuron, isoproturon, metobenzuron, tebuthiuron, dimefuron, isouron, karbutilate, methabenzthiazuron, metoxuron, monolinuron, neburon, siduron, terbumeton, trietazine or metobromuron; a triazine type such as simazine, atrazine, atratone, simetryn, prometryn, dimethametryn, hexazinone, terbuthylazine, cyanazine, ametryn, cybutryne, triaziflam, indaziflam, terbutryn, propazine, metamitron or prometon; a uracil type such as bromacil, bromacyl-lithium, lenacil or terbacil; an anilide type such as propanil or cypromid; a carbamate type such as swep, desmedipham or phenmedipham; a hydroxybenzonitrile type such as bromoxynil, bromoxynil-octanoate, bromoxynil-heptanoate, ioxynil, ioxynil-octanoate, ioxynil-potassium or ioxynil-sodium; and others such as pyridate, bentazone, bentazone-sodium, amicarbazone, methazole or pentanochlor.

(3) Quaternary ammonium salt type such as paraquat or diquat, which is believed to be converted to free radicals by itself to form active oxygen in the plant body and shows rapid herbicidal efficacy.

(4) Those which are believed to exhibit herbicidal effects by inhibiting chlorophyll biosynthesis of plants and abnormally accumulating a photosensitizing peroxide substance in the plant body, such as a diphenylether type such as nitrofen, chlomethoxyfen, bifenox, acifluorfen, acifluorfen-sodium, fomesafen, fomesafen-sodium, oxyfluorfen, lactofen, aclonifen, ethoxyfen-ethyl (HC-252), fluoroglycofen-ethyl or fluoroglycofen; a cyclic imide type such as chlorphthalim, flumioxazin, flumiclorac, flumiclorac-pentyl, cinidon-ethyl, fluthiacet or fluthiacet-methyl; and others such as oxadiargyl, oxadiazon, sulfentrazone, carfentrazone-ethyl, thidiazimin, pentoxazone, azafenidin, isopropazole, pyraflufen-ethyl, benzfendizone, butafenacil, saflufenacil, flupoxam, fluazolate, profluazol, pyraclonil, flufenpyr-ethyl, bencarbazone, ethyl[3-(2-chloro-4-fluoro-5-(3-methyl-2,6-dioxo-4-trifluoromethyl-3,6-dihydro-2H-pyrimidin-1-yl)phenoxy)pyridin-2-yloxy]acetate (SYN-523).

(5) Those which are believed to exhibit herbicidal effects characterized by bleaching activities by inhibiting chromogenesis of plants such as carotenoids, such as a pyridazinone type such as norflurazon, chloridazon or metflurazon; a pyrazole type such as pyrazolynate, pyrazoxyfen, benzofenap, topramezone or pyrasulfotole; and others such as amitrole, fluridone, flurtamone, diflufenican, methoxyphenone, clomazone, sulcotrione, mesotrione, tembotrione, tefuryltrione (AVH-301), bicyclopyrone, isoxaflutole, difenzoquat, difenzoquat-metilsulfate, isoxachlortole, benzobicyclon, picolinafen, beflubutamid, a compound (SW-065, H-965) disclosed in the claim of WO 2003/016286, a compound (KIH-3653, KUH-110) disclosed in the claim of WO 2009/016841, a compound disclosed in the claim of WO 2005/118530, a compound disclosed in the claim of WO 2008/065907, and a compound disclosed in the claim of WO 2009/142318.

(6) Those which exhibit strong herbicidal effects specifically to gramineous plants, such as an aryloxyphenoxypropionic acid type such as diclofop-methyl, diclofop, pyriphenop-sodium, fluazifop-butyl, fluazifop, fluazifop-P, fluazifop-P-butyl, haloxyfop-methyl, haloxyfop, haloxyfop-etotyl, haloxyfop-P, haloxyfop-P-methyl, quizalofop-ethyl, quizalofop-P, quizalofop-P-ethyl, quizalofop-P-tefuryl, cyhalofop-butyl, fenoxaprop-ethyl, fenoxaprop-P, fenoxaprop-P-ethyl, metamifop-propyl, metamifop, clodinafop-propargyl, clodinafop or propaquizafop; a cyclohexanedione type such as alloxydim-sodium, alloxydim, clethodim, sethoxydim, tralkoxydim, butroxydim, tepraloxydim, profoxydim or cycloxydim; and others such as flamprop-M-methyl, flamprop-M or flamprop-M-isopropyl.

(7) Those which are believed to exhibit herbicidal effects by inhibiting an amino acid biosynthesis of plants, such as a sulfonylurea type such as chlorimuron-ethyl, chlorimuron, sulfometuron-methyl, sulfometuron, primisulfuron-methyl, primisulfuron, bensulfuron-methyl, bensulfuron, chlorsulfuron, metsulfuron-methyl, metsulfuron, cinosulfuron, pyrazosulfuron-ethyl, pyrazosulfuron, azimsulfuron, rimsulfuron, nicosulfuron, imazosulfuron, cyclosulfamuron, prosulfuron, flupyrsulfuron-methyl-sodium, flupyrsulfuron, triflusulfuron-methyl, triflusulfuron, halosulfuron-methyl, halosulfuron, thifensulfuron-methyl, thifensulfuron, ethoxysulfuron, oxasulfuron, ethametsulfuron, ethametsulfuron-methyl, iodosulfuron, iodosulfuron-methyl-sodium, sulfosulfuron, triasulfuron, tribenuron-methyl, tribenuron, tritosulfuron, foramsulfuron, trifloxysulfuron, trifloxysulfuron-sodium, mesosulfuron-methyl, mesosulfuron, orthosulfamuron, flucetosulfuron, amidosulfuron, propyrisulfuron (TH-547), metazosulfuron, iofensulfuron, or a compound disclosed in the claim of EP0645386; a triazolopyrimidinesulfonamide type such as flumetsulam, metosulam, diclosulam, cloransulam-methyl, florasulam, penoxsulam or pyroxsulam; an imidazolinone type such as imazapyr, imazapyr-isopropylammonium, imazethapyr, imazethapyr-ammonium, imazaquin, imazaquin-ammonium, imazamox, imazamox-ammonium, imazamethabenz, imazamethabenz-methyl or imazapic; a pyrimidinylsalicylic acid type such as pyrithiobac-sodium, bispyribac-sodium, pyriminobac-methyl, pyribenzoxim, pyriftalid or pyrimisulfan; a sulfonylaminocarbonyltriazolinone type such as flucarbazone, flucarbazone-sodium, propoxycarbazone-sodium, propoxycarbazone or thiencarbazone; and others such as glyphosate, glyphosate-sodium, glyphosate-potassium, glyphosate-ammonium, glyphosate-diammonium, glyphosate-isopropylammonium, glyphosate-trimesium, glyphosate-sesquisodium, glufosinate, glufosinate-ammonium, glufosinate-P, glufosinate-P-ammonium, glufosinate-P-sodium, bilanafos, bilanafos-sodium, cinmethylin or triafamone.

(8) Those which are believed to exhibit herbicidal effects by inhibiting cell mitoses of plants, such as a dinitroaniline type such as trifluralin, oryzalin, nitralin, pendimethalin, ethalfluralin, benfluralin, prodiamine, butralin or dinitramine; an amide type such as bensulide, napropamide, propyzamide or pronamide; an organic phosphorus type such as amiprofos-methyl, butamifos, anilofos or piperophos; a phenyl carbamate type such as propham, chlorpropham, barban or carbetamide; a cumylamine type such as daimuron, cumyluron, bromobutide or methyldymron; and others such as asulam, asulam-sodium, dithiopyr, thiazopyr, chlorthal-dimethyl, chlorthal or diphenamid.

(9) Those which are believed to exhibit herbicidal effects by inhibiting protein biosynthesis or lipid biosynthesis of plants, such as a chloroacetamide type such as alachlor, metazachlor, butachlor, pretilachlor, metolachlor, S-metolachlor, thenylchlor, pethoxamid, acetochlor, propachlor, dimethenamid, dimethenamid-P, propisochlor or dimethachlor a thiocarbamate type such as molinate, dimepiperate, pyributicarb, EPTC, butylate, vemolate, pebulate, cycloate, prosulfocarb, esprocarb, thlobencarb, diallate, tri-allate or orbencarb; and others such as etobenzanid, mefenacet, flufenacet, tridiphane, cafenstrole, fentrazamide, oxaziclomefone, indanofan, benfuresate, pyroxasulfone, fenoxasulfone, dalapon, dalapon-sodium, TCA-sodium or trichloroacetic acid.

(10) MSMA, DSMA, CMA, endothall, endothall-dipotassium, endothall-sodium, endothall-mono(N,N-dimethylalkylammonium), ethofumesate, sodium chlorate, pelargonic acid (nonanoic acid), fosamine, fosamine-ammonium, pinoxaden, ipfencarbazone (HOK-201), aclolein, ammonium sulfamate, borax, chloroacetic acid, sodium chloroacete, cyanamide, methylarsonic acid, dimethylarsinic acid, sodium dimethylarsinate, dinoterb, dinoterb-ammonium, dinoterb-diolamine, dinoterb-acetate, DNOC, ferrous sulfate, flupropanate, flupropanate-sodium, isoxaben, mefluidide, mefluidide-diolamine, metam, metam-ammonium, metam-potassium, metam-sodium, methyl isothiocyanate, pentachlorophenol, sodium pentachlorophenoxide, pentachlorophenol laurate, quinoclamine, sulfuric acid, urea sulfate, methiozolin (MRC-01), etc.

(11) Those which are believed to exhibit herbicidal effects by being parasitic on plants, such as *Xanthomonas campestris, Epicoccisorus nematosorus, Epicoccisorus nematosperus, Exserohilum monoseras* or *Drechsrela monoceras*.

The herbicidal composition of the present invention may be prepared by mixing (a) and (b), as active ingredients, with various agricultural additives in accordance with conventional formulation methods for agricultural chemicals, and applied in various formulations such as dusts, granules, water dispersible granules, wettable powders, tablets, pills, capsules (including a formulation packaged by a water soluble film), water-based suspensions, oil-based suspensions, microemulsions, suspoemulsions, water soluble powders, emulsifiable concentrates, soluble concentrates or pastes. It may be formed into any formulation which is commonly used in this field, so long as the object of the present invention is thereby met.

At the time of the formulation, (a) and (b) may be mixed together for the formulation, or they may be separately formulated.

The additives to be used for the formulation include, for example, a solid carrier such as kaolinite, sericite, diatomaceous earth, slaked lime, calcium carbonate, talc, white carbon, kaoline, bentonite, clay, sodium carbonate, sodium bicarbonate, mirabilite, zeolite or starch; a solvent such as water, toluene, xylene, solvent naphtha, dioxane, dimethylsulfoxide, N,N-dimethylformamide, dimethylacetamide, N-methyl-2-pyrrolidone or an alcohol; an anionic surfactant such as a salt of fatty acid, a benzoate, a polycarboxylate, a salt of alkylsulfuric acid ester, an alkyl sulfate, an alkylaryl sulfate, an alkyl diglycol ether sulfate, a salt of alcohol sulfuric acid ester, an alkyl sulfonate, an alkylaryl sulfonate, an aryl sulfonate, a lignin sulfonate, an alkyldiphenylether disulfonate, a polystyrene sulfonate, a salt of alkylphosphoric acid ester, an alkylaryl phosphate, a styrylaryl phosphate, a salt of polyoxyethylene alkyl ether sulfuric acid ester, a polyoxyethylene alkylaryl ether sulfate, a salt of polyoxyethylene alkylaryl ether sulfuric acid ester, a polyoxyethylene alkyl ether phosphate, a salt of polyoxyethylene alkylaryl phosphoric acid ester, a salt of polyoxyethylene aryl ether phosphoric acid ester, a naphthalene sulfonic acid condensed with formaldehyde or a salt of alkylnaphthalene sulfonic acid condensed with formaldehyde; a nonionic surfactant such as a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, polyethylene glycol, a polyoxyethylene fatty acid ester, a polyoxyethylene sorbitan fatty acid ester, a polyoxyethylene glycerin fatty acid ester, a polyoxyethylene hydrogenated castor oil or a polyoxypropylene fatty acid ester; and a vegetable oil or mineral oil such as olive oil, kapok oil, castor oil, palm oil, camellia oil, coconut oil, sesame oil, corn oil, rice bran oil, peanut oil, cottonseed oil, soybean oil, rapeseed oil, linseed oil, tung oil or liquid paraffins; or transesterified vegetable oil such as methylated rapeseed oil or ethylated rapeseed oil. These additives may suitably be selected for use alone or in combination as a mixture of two or more of them, so long as the object of the present invention is met. Further, additives other than the above-mentioned may be suitably selected for use among those known in this field. For example, various additives commonly used, such as a filler, a thickener, an anti-settling agent, an anti-freezing agent, a dispersion stabilizer, a safener, an anti-mold agent, a bubble agent, a disintegrator and a binder, may be used. The mix ratio by weight of the active ingredient to such various additives in the herbicidal composition of the present invention may be from 0.001: 99.999 to 95:5, preferably from 0.005:99.995 to 90:10.

As a method of applying the herbicidal composition of the present invention, a proper method can be employed among various methods depending upon various conditions such as the application site, the type of the formulation, and the type and the growth stage of the noxious plants to be controlled, and for example, the following methods may be mentioned.

1. (a) and (b) are formulated together, and the formulation is applied as it is.
2. (a) and (b) are formulated together, the formulation is diluted to a predetermined concentration with e.g. water, and as the case requires, a spreader (such as a surfactant, a vegetable oil or a mineral oil) is added for application.
3. (a) and (b) are separately formulated and applied as they are.
4. (a) and (b) are separately formulated, and they are diluted to a predetermined concentration with e.g. water, and as the case requires, a spreader (such as a surfactant, a vegetable oil or a mineral oil) is added for application.
5. (a) and (b) are separately formulated, and the formulations are mixed when diluted to a predetermined concentration with e.g. water, and as the case requires, a spreader (such as a surfactant, a vegetable oil or a mineral oil) is added for application.

EXAMPLES

Now, the present invention will be described in further detail with reference to Examples. However, it should be understood that the present invention is by no means restricted to such specific Examples.

Test Example 1

Upland field soil was put into a 1/1,000,000 hectare pot, and seeds of goosegrass (*Eleusine indica* (L.) Gaertn.) were sown. One day later, water dispersible granules containing flazasulfuron as an active ingredient (tradename: SHIBAGEN DF, manufactured by Ishihara Sangyo Kaisha, Ltd.) and water dispersible granules containing metribuzin as an active ingredient (tradename: Unimark, manufactured by UPL) in predetermined amounts were diluted with water corresponding to 200 L/ha and applied for soil treatment by a small sprayer.

On the 14th day after the treatment, the state of growth of goosegrass was visually observed to determine the growth inhibition rate (%) (measured value) in accordance with the following evaluation standard. Further, in accordance with the Colby's formula, the growth inhibition rate (%) (calculated value) was calculated. The results are shown in Table 1.

Growth inhibition rate(%)=0 (equivalent to the non-treated area) to 100 (complete kill)

TABLE 1

| Active ingredient | Dose (g/ha) | Growth inhibition rate (%) of goosegrass | |
|---|---|---|---|
| | | Measured value | Calculated value |
| Flazasulfuron | 18.75 | 30 | — |
| Metribuzin | 300 | 55 | — |
| | 600 | 73 | — |
| Flazasulfuron + Metribuzin | 18.75 + 300 | 75 | 69 |
| | 18.75 + 600 | 88 | 81 |

Test Example 2

Upland field soil was put into a 1/1,000,000 ha pot, and seeds of goosegrass (*Eleusine indica* (L.) Gaertn.) were sown. When goosegrass reached 5 leaf stage, SHIBAGEN DF (tradename) and Unimark (tradename) in predetermined amounts were diluted with water (corresponding to 200 L/ha) containing 0.25 vol % of an agricultural adjuvant (tradename: Agral, manufactured by Syngenta crop protection) and applied for foliar treatment by a small sprayer.

On the 28th day after the treatment, the state of growth of goosegrass was visually observed, and the growth inhibition rate (%) obtained in the same manner as in Test Example 1 is shown in Table 2.

TABLE 2

| Active ingredient | Dose (g/ha) | Growth inhibition rate (%) of goosegrass | |
|---|---|---|---|
| | | Measured value | Calculated value |
| Flazasulfuron | 37.5 | 25 | — |
| Metribuzin | 800 | 83 | — |
| | 1,000 | 90 | — |
| Flazasulfuron + Metribuzin | 37.5 + 800 | 100 | 87 |
| | 37.5 + 1,000 | 100 | 93 |

Test Example 3

Upland field soil was put into a 1/1,000,000 ha pot, and seeds of ivy-leaved morningglory (*Ipomoea hederacea* (L.) Jacq.) were sown. On the next day, SHIBAGEN DF (tradename) and Unimark (tradename) in predetermined amounts were diluted with water corresponding to 300 L/ha and applied for foliar treatment by a small sprayer.

On the 14th day after the treatment, the state of growth of ivy-leaved morningglory was visually observed, and the growth inhibition rate (%) obtained in the same manner as in Test Example 1 is shown in Table 3.

TABLE 3

| Active ingredient | Dose (g/ha) | Growth inhibition rate (%) of ivy-leaved morningglory | |
|---|---|---|---|
| | | Measured value | Calculated value |
| Flazasulfuron | 100 | 80 | — |
| Metribuzin | 300 | 0 | — |
| Flazasulfuron + Metribuzin | 100 + 300 | 85 | 80 |

Test Example 4

Upland field soil was put into a 1/1,000,000 ha pot, and seeds of shattercane (*Sorghum bicolor* (L.) Moench.) were sown. On the next day, SHIBAGEN DF (tradename) and Unimark (tradename) in predetermined amounts were diluted with water corresponding to 300 L/ha and applied for soil treatment by a small sprayer.

On the 14th day after the treatment, the state of growth of shattercane was visually observed, and the growth inhibition rate (%) obtained in the same manner as in Test Example 1 is shown in Table 4.

TABLE 4

| Active ingredient | Dose (g/ha) | Growth inhibition rate (%) of shattercane | |
|---|---|---|---|
| | | Measured value | Calculated value |
| Flazasulfuron | 15 | 30 | — |
| Metribuzin | 2,000 | 20 | — |
| Flazasulfuron + Metribuzin | 15 + 2,000 | 83 | 44 |

Test Example 5

In a field in which summergrass (*Digitaria ciliaris* (Retz.) Koel), giant foxtail (*Setaria faberi* Herrm.), redroot pigweed (*Amaranthus retroflexus* L.) and threeseeded copperleaf (*Acalypha australis* L.) emerged, was compartmentalized into compartments of 0.5×1 m. When summergrass reached from 5 to 10 leaf stage, giant foxtail reached from 6 to 7 leaf stage, threeseeded copperleaf reached from 4 to 10 leaf stage and redroot pigweed reached from 6 to 9 leaf stage, SHIBA-GEN DF (tradename) and Unimark (tradename) in predetermined amounts were diluted with water (corresponding to 200 L/ha) containing 0.25 vol % of an agricultural adjuvant Agral (tradename) and applied for foliar treatment by a small sprayer in each compartment.

On the 6th, 20th and 33rd days after the treatment, the weed coverage (%) of the above four types of weeds in each compartment was visually observed, and the results are shown in Table 5 and FIG. 1. The weed coverage (%) was calculated in accordance with the following formula.

A: (the area of the ground surface covered with the weed aerial part (leaves and stem) in the treated area)
B: (the area of the ground surface covered with the weed aerial part (leaves and stem) in the non-treated area)

Weed coverage(%)=(A/B)×100

In FIG. 1, x-x represents the weed coverage in the area treated with flazasulfuron, ▲-▲ represents the weed coverage in the area treated with metribuzin, and ●-● represents the weed coverage in the area treated with flazasulfuron and metribuzin in combination.

TABLE 5

| Active ingredient | Dose (g/ha) | Weed coverage (%) | | |
|---|---|---|---|---|
| | | 6th day after treatment | 20th day after treatment | 33rd day after treatment |
| Flazasulfuron | 37.5 | 26 | 30 | 65 |
| Metribuzin | 1,200 | 19 | 24 | 35 |
| Flazasulfuron + Metribuzin | 37.5 + 800 | 11 | 11 | 12 |

In the area treated with flazasulfuron and in the area treated with metribuzin, an increase in the weed coverage was confirmed on the 20th day after the treatment, whereas in the area treated with flazasulfuron and metribuzin in combination, the weed coverage was not substantially increased even in the observation on the 33rd day after the treatment, although the dose of metribuzin was reduced. Accordingly, it is found that by use of flazasulfuron and metribuzin in combination, the residual activity is remarkably improved as compared with a case where the respective active ingredients are applied individually.

INDUSTRIAL APPLICABILITY

According to the present invention, it is possible to provide a herbicidal composition which has a broad herbicidal spectrum and also has a high activity and a remarkably improved residual activity.

The entire disclosure of Japanese Patent Application No. 2011-090116 filed on Apr. 14, 2011 including specification, claims, drawings and summary is incorporated herein by reference in its entirety.

The invention claimed is:

1. A herbicidal composition comprising, as active ingredients, (a) flazasulfuron or its salt and (b) metribuzin or its salt.

2. The herbicidal composition according to claim 1, wherein the mixing ratio of (a) to (b) is from 1:300 to 1:1 by the weight ratio.

3. A method for controlling noxious plants, which comprises applying a herbicidally effective amount of a herbicidal composition comprising, as active ingredients, (a) flazasulfuron or its salt and (b) metribuzin or its salt, to the noxious plants or to a place where they grow.

4. The method according to claim 3, wherein (a) is applied in an amount of from 10 to 200 g/ha, and (b) is applied in an amount of from 200 to 3,000 g/ha.

5. A method for controlling noxious plants, which comprises applying a herbicidally effective amount of (a) flazasulfuron or its salt, and a herbicidally effective amount of (b) metribuzin or its salt, to the noxious plants or to a place where they grow.

6. The method according to claim 5, wherein (a) is applied in an amount of from 10 to 200 g/ha, and (b) is applied in an amount of from 200 to 3,000 g/ha.

* * * * *